US009828482B2

(12) United States Patent
Gawryla (10) Patent No.: US 9,828,482 B2
(45) Date of Patent: Nov. 28, 2017

(54) REVERSIBLY CROSS-LINKABLE RESIN

(71) Applicant: Owens Corning Intellectual Capital, LLC, Toledo, OH (US)

(72) Inventor: Matthew Daniel Gawryla, Chagrin Falls, OH (US)

(73) Assignee: Owens Corning Intellectual Capital, LLC, Toledo, OH (US)

( * ) Notice: Subject to any disclaimer, the term of this patent is extended or adjusted under 35 U.S.C. 154(b) by 22 days.

(21) Appl. No.: 14/748,388

(22) Filed: Jun. 24, 2015

(65) Prior Publication Data

US 2015/0368422 A1 Dec. 24, 2015

Related U.S. Application Data

(60) Provisional application No. 62/016,233, filed on Jun. 24, 2014.

(51) Int. Cl.
*C08J 9/14* (2006.01)
*C08J 9/12* (2006.01)
(Continued)

(52) U.S. Cl.
CPC .............. *C08J 9/144* (2013.01); *C08J 9/008* (2013.01); *C08J 9/0019* (2013.01); *C08J 9/0061* (2013.01); *C08J 9/0095* (2013.01); *C08J 9/122* (2013.01); *C08J 9/146* (2013.01); *B01J 31/165* (2013.01); *C07D 471/12* (2013.01); *C08J 2201/026* (2013.01); *C08J 2201/03* (2013.01); *C08J 2203/06* (2013.01); *C08J 2203/142* (2013.01);
(Continued)

(58) Field of Classification Search
CPC ................... C08J 3/24; B01J 31/165
See application file for complete search history.

(56) References Cited

U.S. PATENT DOCUMENTS

| 4,187,353 A * | 2/1980 | Schroeder | C08J 5/12 |
| | | | 521/149 |
| 4,694,025 A * | 9/1987 | Park | C08J 9/0023 |
| | | | 521/134 |

(Continued)

FOREIGN PATENT DOCUMENTS

| JP | 20010181222 | 3/2001 |
| WO | 2005/063895 | 7/2005 |

OTHER PUBLICATIONS

Haras, A.; Anderson, G.D.W.; Michalak, A.; Rieger, B.; Ziegler, T. Computational insight into catalytic control of poly(ethylene-methyl acrylate) topology. Organometallics, 2006, 25, 4491-4497.*

(Continued)

*Primary Examiner* — Mike M Dollinger
*Assistant Examiner* — Christina Wales
(74) *Attorney, Agent, or Firm* — Calfee, Halter & Griswold LLP (57) ABSTRACT

Reversibly cross-linkable foam is provided. The reversibly cross-linked foam includes a first polymeric material, at least one reversibly cross-linkable monomer polymerized with the first polymeric material, and at least one blowing agent. The reversibly cross-linkable co-polymeric foam is thermally stable at temperatures of at least 10 degrees higher than otherwise identical polymeric foam that does not include the reversibly cross-linkable agent polymerized with the first polymeric material.

18 Claims, 3 Drawing Sheets

(51) Int. Cl.
*C08J 9/00* (2006.01)
*B01J 31/16* (2006.01)
*C07D 471/12* (2006.01)

(52) U.S. Cl.
CPC .... *C08J 2203/162* (2013.01); *C08J 2205/052* (2013.01); *C08J 2205/10* (2013.01); *C08J 2300/30* (2013.01); *C08J 2325/08* (2013.01)

(56) References Cited

U.S. PATENT DOCUMENTS

| | | | | |
|---|---|---|---|---|
| 6,174,929 | B1* | 1/2001 | Hahnle | A61L 15/425 521/149 |
| 6,207,762 | B1 | 3/2001 | Kobayashi et al. | |
| 6,380,278 | B1 | 4/2002 | Fan et al. | |
| 6,506,807 | B1* | 1/2003 | Yanagihara | B29C 44/3461 264/37.18 |
| 2003/0204019 | A1* | 10/2003 | Ding | C08L 53/025 525/191 |
| 2004/0039094 | A1* | 2/2004 | Taylor | C08F 290/14 524/261 |
| 2006/0041044 | A1 | 2/2006 | Husemann et al. | |
| 2007/0149711 | A1* | 6/2007 | Chaudhary | C08F 8/00 525/244 |
| 2008/0293878 | A1* | 11/2008 | Funk | C08G 77/58 524/588 |
| 2012/0264840 | A1* | 10/2012 | Klein | C08G 18/3893 521/111 |

OTHER PUBLICATIONS

Fang, S.M.; Wang, C.; Hu, M.; Wang, P.Y.; Zhou, L.M.; Gao, L.J.; Liu, C.S. Preparation and characterization of a series of novel EuIII-complex-polyurethane acrylate materials based on mixed 6-hydroxy-1-naphthoate and 1,10-phenanthroline ligands. J app poly sci 2012, 3404-3409.*

Hofmeir, H.; El-ghayoury, A.; Schubert, U.S. Combination of supramolecular cross-linking with covalent cross-linking through epoxide ring-opening including gel studies. e-Polymers 2003 p. 1-13.*

"Foaming Plastics with Inert Gases" by Carl Hanser Verlag. Kunstoffe plast europe Jun. 2005. p. 1-4.*

Bailey, et al. "Novel Metal Containing Crosslinkers for High Solids and Hot Melt Acrylic Pressure Sensitive Adhesives—The Benefits of Reversible Crosslinking", Saratomer Company, 6 pgs., dated at least as early as the filing date of this application.

Bergman et al., "Mendable polymers", J. of Materials Chemistry, 18, pp. 41-62 (2008).

McKenzie et al., "Improved synthesis of functionalized mesogenic 2,6-bisbenzimidazolylpyridine ligands", Tetrahedron, 64, pp. 8488-8495 (2008).

Liu et al, "Thermally reversible cross-linked polyamides and thermo-responsive gels by means of Diels-Alder reaction", Polymer 47, pp. 2581-2586 (2006).

* cited by examiner

REVERSIBLY CROSS-LINKABLE RESIN

RELATED APPLICATIONS

This application claims the benefit of U.S. provisional application No. 62/016,233 filed on Jun. 24, 2014, titled "Reversibly Cross-Linkable Resin" which is incorporated herein by reference in its entirety.

BACKGROUND

Extruded synthetic foam is generally prepared by melting a base polymeric composition and incorporating one or more blowing agents and optional additives into the polymeric melt under conditions that provide for the thorough mixing of the blowing agent and the polymer while preventing the mixture from foaming prematurely, e.g., under pressure. This mixture may then be extruded through a single or multi-stage extrusion die to cool and reduce the pressure on the mixture, allowing the mixture to foam and produce a foamed product.

Polystyrene is often used to produce foams, since polystyrene foams are good thermal insulators. Polystyrene foams are traditionally less thermally stable at high temperatures than other foamed polymers, which limit the use of polystyrene foams in certain markets.

U.S. 2007/0149711 ('771) discloses a polymeric composition that includes thermally reversible cross-linked bonds. The thermally reversible cross-links are formed by mixing a free-radical reactive polymer, such as polyethylene; a free-radical inducing species; a free radical trapping species; and a complementary thermal-reversible bond contributor. The polymer is capable of forming free radicals when induced by the free radical inducing species.

BRIEF SUMMARY

Various exemplary aspects of the general inventive concepts are directed to reversibly cross-linked polymeric foam. The reversibly cross-linked polymeric foam includes a first polymeric material, at least one reversibly cross-linkable agent polymerized with the first polymer material, and at least one blowing agent. In some exemplary embodiments, the reversibly cross-linked polymeric foam is thermally stable at temperatures of at least 10° F. higher than otherwise identical polymeric foam that does not include the reversibly cross-linkable agent copolymerized with the polymeric material.

Other exemplary aspects of the general inventive concepts are directed to a method of manufacturing extruded reversibly cross-linked polymeric foam. The method includes introducing a foamable polymeric composition into an extruder to form a polymer melt, injecting at least one blowing agent into the polymer melt, and extruding the polymer melt to produce polymeric foam. The foamable polymeric composition includes a first polymeric material and at least one reversibly cross-linkable monomer copolymerized with the polymer material;

Yet other exemplary aspects of the general inventive concepts are directed to a reversibly cross-linkable foamable mixture. The reversibly cross-linked foamable mixture includes a first polymeric material and at least one reversibly cross-linkable agent polymerized with the first polymeric material. The reversibly cross-linkable foamable mixture is capable of forming extruded, reversibly cross-linked polymeric foam.

The foregoing and other objects, features, and advantages of the general inventive concepts will become more readily apparent from a consideration of the detailed description that follows.

DESCRIPTION OF THE DRAWINGS

Example embodiments of the invention will be apparent from the more particular description of certain example embodiments of the invention provided below and as illustrated in the accompanying drawings.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including published or corresponding U.S. or foreign patent applications, issued U.S. or foreign patents, or any other references, are each incorporated by reference in their entireties, including all data, tables, figures, and text presented in the cited references. In the drawings, the thickness of the lines, layers, and regions may be exaggerated for clarity. It is to be noted that like numbers found throughout the figures denote like elements. The terms "composition" and "inventive composition" may be used interchangeably herein.

The present invention relates to reversibly cross-linked copolymer extruded or expanded foams that contain cross-linking monomers or polymers polymerized with a first polymeric material, forming a reversibly cross-linkable foamable material. The particular first polymeric material may be selected to provide sufficient mechanical strength and/or to the process utilized to form final foamed polymeric products. In addition, the first polymeric material is preferably chemically stable, i.e., generally non-reactive, within the expected temperature range during formation and subsequent use in a polymeric foam.

The first polymeric material is not particularly limited and may include any polymer conventionally used in the art. As used herein, the term "polymer" is generic to the terms "homopolymer," "copolymer," "terpolymer," and combinations of homopolymers, copolymers, and/or terpolymers. Non-limiting examples of suitable foamable polymers include alkenyl aromatic polymers, polyvinyl chloride ("PVC"), chlorinated polyvinyl chloride ("CPVC"), polyethylene, polypropylene, polycarbonates, polyisocyanurates, polyetherimides, polyamides, polyesters, polycarbonates, polymethylmethacrylate, polyphenylene oxide, polyurethanes, phenolics, polyolefins, styrene acrylonitrile ("SAN"), acrylonitrile butadiene styrene, acrylic/styrene/acrylonitrile block terpolymer ("ASA"), polysulfone, polyurethane, polyphenylene sulfide, acetal resins, polyamides, polyaramides, polyimides, polyacrylic acid esters, copolymers of ethylene and propylene, copolymers of styrene and butadiene, copolymers of vinylacetate and ethylene, rubber modified polymers, thermoplastic polymer blends, and combinations thereof.

In one exemplary embodiment, the first polymeric composition is an alkenyl aromatic polymer material. Suitable alkenyl aromatic polymer materials include alkenyl aromatic homopolymers and copolymers of alkenyl aromatic compounds and copolymerizable ethylenically unsaturated co-monomers. In addition, the alkenyl aromatic polymer material may include minor proportions of non-alkenyl aromatic polymers. The alkenyl aromatic polymer material may be formed of one or more alkenyl aromatic homopolymers, one or more alkenyl aromatic copolymers, a blend of one or more of each of alkenyl aromatic homopolymers and copolymers, or blends thereof with a non-alkenyl aromatic polymer.

Examples of alkenyl aromatic polymers include, but are not limited to, those alkenyl aromatic polymers derived from alkenyl aromatic compounds such as styrene, alpha-methylstyrene, ethylstyrene, vinyl benzene, vinyl toluene, chlorostyrene, and bromostyrene. In at least one embodiment, the alkenyl aromatic polymer is polystyrene.

In certain exemplary embodiments, minor amounts of monoethylenically unsaturated monomers such as $C_2$ to $C_6$ alkyl acids and esters, ionomeric derivatives, and $C_2$ to $C_6$ dienes may be copolymerized with alkenyl aromatic monomers to form the alkenyl aromatic polymer. Non-limiting examples of copolymerizable monomers include acrylic acid, methacrylic acid, ethacrylic acid, maleic acid, itaconic acid, acrylonitrile, maleic anhydride, methyl acrylate, ethyl acrylate, isobutyl acrylate, n-butyl acrylate, methyl methacrylate, vinyl acetate and butadiene.

The first polymeric material may be present in the composition in an amount from about 50 to about 95 mol % based on the total monomers present in the foamable composition. In other exemplary embodiments, the first polymeric material is present in an amount from about 75 to about 85 mol %, based on the total monomers present in the foamable composition.

In some exemplary embodiments, the first polymeric material is blended with one or more cross-linking agents, forming a reversibly cross-linkable copolymer. The cross-links may be reversible by heating the polymeric material to an elevated temperature that breaks the cross-links, allowing the material to be melted down to form a flowable material that may be recycled or reused, if desired. The cross-links may then be re-formed when the temperature is then lowered to a particular service temperature.

In some exemplary embodiments, the cross-linking agents comprise complex ions. The complex ions may comprise a metal cation with one or more ligands covalently bonded thereto. The metal-ligand complex is able to copolymerize with the monomer, such as styrene, to form reversible ionic linkages in the polymer backbone forming the first polymeric material.

In some exemplary embodiments, the reversible cross-linking agent comprises monomers that may undergo cross-linking via a Diels-Alder reaction. Such compositions include, for example, furan-maleimide moieties, cyclopentadiene moieties, anthracene-meleimide pendent groups. The polymers containing furan and maleimide pendent groups are then reversibly cross-linked through a Diels-Alder reaction. However, upon heating the polymer, the two monomers may be regenerated via a retro-Diels-Alder reaction. Cooling the two starting monomers to room temperature for an extended period, such as 7 days, may reform the cross-linked polymer.

In some exemplary embodiments, the reversible cross-linking is achieved by employing multiple hydrogen bonds, which may create a reversible supramolecular polymer network. For example, the polymer material may include 2-uriedo-4-pyrimodone end groups that form dimers held together by quadruple hydrogen bonds. Another example includes supramolecular polymers based on bis(melamine) that can non-covalently polymerize upon binding with cyanurates, barbiturates through complementary triple hydrogen-bonding interaction.

In some exemplary embodiments, the reversible cross-linking is achieved by using a hybrid covalent/non-covalent system. The hybrid system may include a polyrotaxane network with reversibly cross-linked thiol-disulfide bridges. Under reducing condition, the disulfide (SS) bridges in the polymer breaks and results in monomers, however, under oxidizing condition, the thiols of each monomer forms the disulfide bond, cross-linking the starting materials to form the polymer. Alternatively, the monomeric units, m-phenylene ethylene oligomers, may be covalently bound to each other In the case of metal-ligand complexes as the reversibly cross-linking material, metal salts of alpha-beta ethylenically unsaturated carboxylic acids may be formed, described by the general structure below:

Where
R=H or $CH_3$
R'=an organic moiety such as polyester or urethane
M=Zn, Ca, Mg, etc.

The metal-ligand complex may be produced by reacting one or more polyisocyanates, one or more hydroxy functional (meth)acrylates, and one or more metal salt polyols. The metal salt polyols may be formed as the reaction product of a metal oxide and a half ester containing a hydroxy group and a carboxylic acid group. The metal salt polyol(s) can be mixed and reacted with a molar excess of the polyisocyanate(s) followed by reacting the resultant isocyanato-terminated product with the hydroxy functional (meth) acrylate(s), or in an alternative method the polyisocyanate(s), hydroxy functional (meth)acrylate(s), and metal salt polyol(s) can be mixed and reacted in one step.

Suitable metals for use in the metal-ligand complex may include, for example, magnesium, calcium, strontium, barium, titanium, zirconium, vanadium, chromium, molybdenum, tungsten, manganese, iron, cobalt, nickel, palladium, copper, zinc, boron, aluminum, gallium, indium, silicon, germanium, tin, lead, antimony, bismuth, and the like. In some exemplary embodiment, the metal may be an anhydride, oxide, halide, alkoxide, hydroxide, nitrate, sulfate, carboxylate, and carbonate. In some exemplary embodiments, the metal compound is zinc oxide.

Suitable polyols include diols such as ethylene glycol, propylene glycol, 1,3-propanediol, 1,2, 1,3 or 1,4 butanediols, 2-methyl-1,3-propane diol (MPDiol), neopentyl glycol (NPG), alkoxylated derivatives of such diols, polyether diols, polyester diols, and the like. Suitable higher functional polyols are trimethylol propane (TMP), PETA, di-TMP, di-PETA, glycerol, alkoxylated derivatives thereof, and the like.

Exemplary hydroxyl-containing (meth)acrylates include hydroxyethyl (meth)acrylate, hydroxypropyl (meth)acrylate, hydroxybutyl (meth)acrylate, trimethylolpropane mono- and di-(meth)acrylate, pentaerythritol mono-, di-, tri-(meth)acrylate, dipentaerythritol mono-, di-, tri-, tetra-, and penta-(meth)acrylate, neopentyl glycol (meth)acrylate, hexanediol mono(meth)acrylate, tris(2-hydroxyethyl)isocyanurate mono- and di(meth)acrylate, polypropylene glycol mono(meth)acrylate, polyethylene glycol mono (meth) acrylate, polypropylene/polyethylene glycol mono(meth)acrylate, polybutyl glycol mono(meth)acrylate, polytetramethylene glycol mono(meth)acrylate, hydroxy polycaprolacton mono(meth)acrylate, and ethoxylated and propoxylated derivatives thereof.

Some of the polyisocyanate examples are hexamethylene diisocyanate, isophorone diisocyanate, cyclohexane-1,4-diisocyanate, methylene bis(4-cyclohexylisocyanate), toluene diisocyanate, diphenylmethane 4,4-diisocyanate, xylene diisocyanate, 1,4-phenylene diisocyanate, diisocyanates and triisocyanates of HDI-based oligomers, and other aliphatic and aromatic isocyanates.

Alternatively, the metal-ligand complex may be produced using a terpyridine ligand reacted with a metal ion to fabricate metallo-supramolecular polymers. For example, a terdentate ligand 2,6-bis(benximidazolyl)-4-oxypyridine to the ends of macromonomer units, followed by complexation with a metal ion, such as Fe(II), Co(II), Zn(II), or Cd (II).

In some exemplary embodiments, the reversibly cross-linkable copolymer is blended with a second polymeric material. The particular second polymeric material may be selected to provide sufficient mechanical strength and/or to the process utilized to foul' final foamed polymeric products. In addition, the second polymeric material is preferably chemically stable, i.e., generally non-reactive, within the expected temperature range during formation and subsequent use in a polymeric foam.

The second polymeric material is not particularly limited and may include any polymeric conventionally used in the art. Non-limiting examples of suitable second polymers include alkenyl aromatic polymers, polyvinyl chloride ("PVC"), chlorinated polyvinyl chloride ("CPVC"), polyethylene, polypropylene, polycarbonates, polyisocyanurates, polyetherimides, polyamides, polyesters, polycarbonates, polymethylmethacrylate, polyphenylene oxide, polyurethanes, phenolics, polyolefins, styrene acrylonitrile ("SAN"), acrylonitrile butadiene styrene, acrylic/styrene/acrylonitrile block terpolymer ("ASA"), polysulfone, polyurethane, polyphenylene sulfide, acetal resins, polyamides, polyaramides, polyimides, polyacrylic acid esters, copolymers of ethylene and propylene, copolymers of styrene and butadiene, copolymers of vinylacetate and ethylene, rubber modified polymers, thermoplastic polymer blends, and combinations thereof.

In one exemplary embodiment, the second polymeric composition is an alkenyl aromatic polymer material. Suitable alkenyl aromatic polymer materials include alkenyl aromatic homopolymers and copolymers of alkenyl aromatic compounds and copolymerizable ethylenically unsaturated co-monomers. In addition, the alkenyl aromatic polymer material may include minor proportions of non-alkenyl aromatic polymers. The alkenyl aromatic polymer material may be formed of one or more alkenyl aromatic homopolymers, one or more alkenyl aromatic copolymers, a blend of one or more of each of alkenyl aromatic homopolymers and copolymers, or blends thereof with a non-alkenyl aromatic polymer.

Examples of alkenyl aromatic polymers include, but are not limited to, those alkenyl aromatic polymers derived from alkenyl aromatic compounds such as styrene, alpha-methylstyrene, ethylstyrene, vinyl benzene, vinyl toluene, chlorostyrene, and bromostyrene. In at least one embodiment, the alkenyl aromatic polymer is polystyrene.

In certain exemplary embodiments, minor amounts of monoethylenically unsaturated monomers such as $C_2$ to $C_6$ alkyl acids and esters, ionomeric derivatives, and $C_2$ to $C_6$ dienes may be copolymerized with alkenyl aromatic monomers to form the alkenyl aromatic polymer. Non-limiting examples of copolymerizable monomers include acrylic acid, methacrylic acid, ethacrylic acid, maleic acid, itaconic acid, acrylonitrile, maleic anhydride, methyl acrylate, ethyl acrylate, isobutyl acrylate, n-butyl acrylate, methyl methacrylate, vinyl acetate and butadiene.

The second polymeric material may be present in the composition in an amount from about 50 to about 95 mol % based on the total amount of copolymers present in the foamable composition. In other exemplary embodiments, the polymeric material is present in an amount from about 75 to about 85 mol %, based on the total monomers present in the foamable composition.

In some exemplary embodiments, the reversibly cross-linkable copolymer may contain about 50 mol % to 100 mol % of a first copolymer made of between 5 mol % and 50 mol % cross-linkable monomer. The reversibly cross-linkable copolymer further includes a second polymeric material present in amounts between 5 mol % and 50 mol %, or between about 10 mol % and 40 mol %, or between 20 mol % and 40 mol %. An exemplary foamable composition may comprise a first copolymer, comprising a blend of polystyrene and a reversible cross-linker (present in 5 mol %-50 mol %), which is then blended with polystyrene at concentrations between 5 mol % and 50 mol %. In some exemplary embodiments, the second polymeric material is polyethylene The reversible cross-linking may occur with or without the use of a catalyst. When a catalyst is used, any conventional catalyst may be used for the particular cross-linking mechanism. The use of a catalyst may shorten the reaction time and produce fewer by-products.

The present invention relates to polymeric foam and polymeric foam products, such as extruded or expanded foams, formed from a composition that contains a reversibly cross-linking monomer or polymer blended with a first polymeric material, such as polystyrene, forming a reversibly cross-linkable copolymer. Optionally, the reversibly cross-linkable copolymer may be further blended with a second polymeric material. The polymeric foamable material further includes at least one blowing agent (for example, hydrofluorocarbons (HFCs), hydrofluoroolefins (HFOs), hydrochlorofluoroolefins (HCFO), carbon dioxide ($CO_2$), nitrogen, argon, alcohols, ethers, or mixtures thereof). As used herein, the term "blowing agent" is understood to include physical (e.g., dissolved gaseous agents) or chemical blowing agents (e.g., a gas generated by decomposition). A blowing agent is generally added to a molten polymer, e.g., in an extruder, and under the proper conditions, to initiate foaming to produce a foamed thermoplastic. The blowing agent expands the resin and forms cells (e.g., open or closed pores). As the resin hardens or cures, foam is produced with either the blowing agent trapped in the cells or ambient air displaces the blowing agent in the cells.

The blowing agent may be introduced in liquid or gaseous form (e.g., a physical blowing agent) or may be generated in situ while producing the foam (e.g., a chemical blowing agent). For instance, the blowing agent may be formed by decomposition of another constituent during production of the foamed thermoplastic. For example, in the case of a blowing agent that comprises $CO_2$, a carbonate composition or polycarbonic acid may be added to the foamable resin and carbon dioxide will be generated upon heating during the extrusion process.

In some exemplary embodiments, the blowing agent may be present in the foamable polymeric composition in an amount from about 1.0 to 15.0 weight percent, or from about 2.0 to 10 weight percent of the foamable composition. In some exemplary embodiments, halogenated blowing agents are present in an amount from about 6.0 to 10.0 weight percent of the foamable polymeric composition and non-halogenated blowing agents are present in an amount from about 2.0 to 5.0 weight percent of the foamable polymeric composition.

The foamable composition may further contain at least one infrared attenuating agent (IAA). Blowing agents such as HFCs and HFOs, while environmentally friendly, tend to decrease the R-value of the foam product compared to a conventional foamed product. The addition of low levels of an infrared attenuating agent to a foamable composition containing such blowing agents may increase the R-value of the foam to an amount at least comparable to, or better than, foam produced with conventional blowing agents. Although the infrared attenuating agent increases the R-value for foams that include HFO and/or HFC blowing agents, the addition of infrared attenuating agents also tends to decrease the cell size of the cells in the foam, which results in undesirable final foamed products including higher density and product cost. Therefore, the IAA should be included in no more than about 0.005% to 5.0% by weight of the total composition. In other embodiments, the infrared attenuating agent may be present in an amount from 0.05 to 3.0% by weight, from 0.05 to 2.0% by weight, or from 0.1 to 1.0% by weight. In some exemplary embodiments, the infrared attenuating agent is present in the composition in an amount less than or equal to 0.5% by weight.

Non-limiting examples of suitable IAAs for use in the present composition include nanographite, carbon black, powdered amorphous carbon, asphalt, granulated asphalt, milled glass, fiber glass strands, mica, dyes, black iron oxide, metal flakes (for example, aluminum flakes), carbon nanotube, nanographene platelets, carbon nanofiber, activated carbon, titanium dioxide, other organic IAAs, and combinations thereof.

In at least one exemplary embodiment, the IAA is nanographite. The nanographite can be multilayered by furnace high temperature expansion from acid-treated natural graphite or microwave heating expansion from moisture saturated natural graphite. In addition, the nanographite may be multi-layered nanographite which has at least one dimension less than 100 nm. In some exemplary embodiments, the nanographite has at least two dimensions less than 100 nm.

The nanographite may or may not be chemically or surface modified and may be compounded in a polyethylene methyl acrylate copolymer (EMA), which is used both as a medium and a carrier for the nanographite. Other possible carriers for the nanographite include polymer carriers such as, but not limited to, polymethyl methacrylate (PMMA), polystyrene, polyvinyl alcohol (PVOH), and polyvinyl acetate (PVA). In exemplary embodiments, the nanographite is substantially evenly distributed throughout the foam. As used herein, the phrase "substantially evenly distributed" is meant to indicate that the substance (for example, nanographite) is evenly distributed or nearly evenly distributed within the foam.

The polymeric foam composition may further contain a fire retarding agent in about 1.0% or more by weight. For example, fire retardant chemicals may be added in the extruded foam manufacturing process to impart fire retardant characteristics to the extruded foam products. Non-limiting examples of suitable fire retardant chemicals for use in the inventive composition include brominated aliphatic compounds such as hexabromocyclododecane and pentabromocyclohexane, brominated phenyl ethers, esters of tetrabromophthalic acid, halogenated polymeric flame retardant such as brominated polymeric flame retardant and combinations thereof.

Optional additives such as nucleating agents, plasticizing agents, pigments, elastomers, extrusion aids, antioxidants, fillers, antistatic agents, biocides, and/or UV absorbers may be incorporated into the inventive composition. These optional additives may be included in amounts necessary to obtain desired characteristics of the foamable gel or resultant extruded foam products. The additives may be added to the polymer mixture or they may be incorporated in the polymer mixture before, during, or after the polymerization process used to make the polymer.

The present invention further relates to a method for manufacturing a reversibly cross-linked polymeric foamable material, polymeric foam, or foam product. Unlike conventional covalent cross-linking between polymer materials and cross-linking agents, the reversible cross-links disclosed herein can be broken and reformed. The ability to reverse cross-linking allows for the reuse of scrap material and efficient foam recycling.

Figure 1:
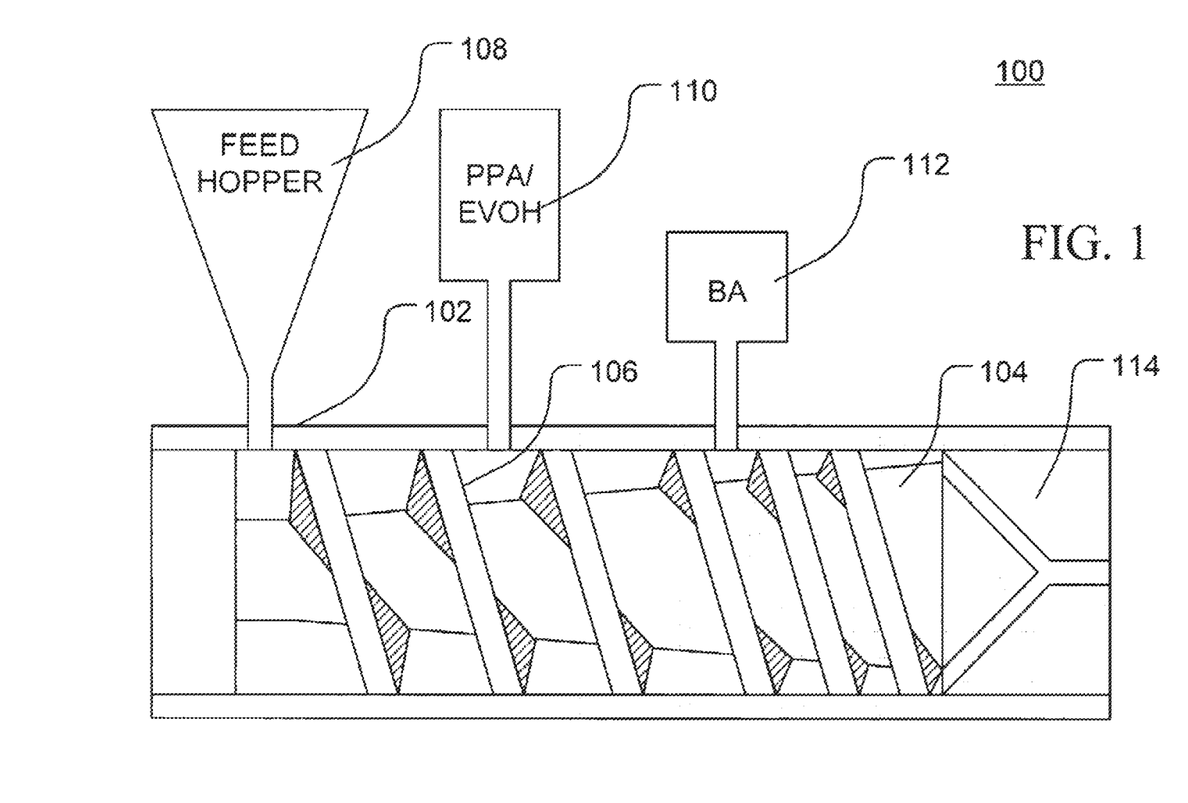
FIG. 1 is a schematic drawing of an exemplary extrusion apparatus useful for practicing methods according to the invention.

FIG. 1 illustrates an exemplary extrusion apparatus 100 useful for practicing methods according to the present invention. The extrusion apparatus 100 may comprise a single or double (not shown) screw extruder including a barrel 102 surrounding a screw 104 on which a spiral flight 106 is provided, configured to compress, and thereby, heat material introduced into the screw extruder. The reversibly cross-linkable monomer or polymer material may be premixed with the first polymeric material, such as polystyrene, prior to feeding the material into the screw extruder, forming a reversibly cross-linkable copolymer. In some exemplary embodiments, the reversibly cross-linkable copolymer is further blended with a second polymeric material, which may be the same polymer as the first polymeric material, or may comprise a different polymeric material.

The reversibly cross-linkable foamable composition, comprising either the cross-linkable co-polymer independently or the cross-linkable co-polymer blended with a second polymeric material, may be feed into the screw extruder as a flowable solid, such as beads, granules or pellets, or as a liquid or semi-liquid melt, from one or more feed hoppers 108.

As the reversibly cross-linkable foamable composition advances through the screw extruder 100, the decreasing spacing of the flight 106, defines a successively smaller space through which the copolymer composition is forced by the rotation of the screw. This decreasing volume acts to increase the temperature of the reversibly cross-linkable foamable composition to a critical temperature that is below melt temperature of the process, at which time the reversible cross-links are broken to obtain a polymeric melt (if solid starting material was used) and/or to increase the temperature of the polymeric melt.

One or more ports may be provided through the barrel 102 with associated apparatus 110 configured for injecting one or more processing aids into the polymer composition. Similarly, one or more ports may be provided through the barrel 102 with associated apparatus 112 for injecting one or more blowing agents into the reversibly cross-linkable foamable composition. Once the blowing agent(s) and optional polymer processing aid(s) have been introduced into the reversibly cross-linkable foamable composition, the resulting mixture is subjected to some additional blending sufficient to distribute each of the additives generally uniformly throughout the reversibly cross-linkable foamable composition to obtain an extrusion composition.

This extrusion composition is then forced through an extrusion die 114 and exits the die into a region of reduced pressure (which may be above, or more typically below atmospheric pressure), thereby allowing the blowing agent to expand and produce a polymeric foam layer or slab. This pressure reduction may be obtained gradually as the extruded polymeric mixture advances through successively larger openings provided in the die or through some suitable apparatus (not shown) provided downstream of the extrusion die for controlling to some degree the manner in which the pressure applied to the polymeric mixture is reduced. The polymeric foam may also be subjected to additional processing such as calendaring, water immersion, cooling sprays or other operations to control the thickness and other properties of the resulting polymeric foam product. The cross-linkable monomer or polymer present in the polymeric material, will crosslink upon cooling the molten polymer below a critical temperature, which is dependent on the particular monomer used and cross-linking chemistry.

In some exemplary embodiments, the temperature of the polymeric melt is lowered to a point near the cross-linking critical temperature while the polymeric melt is still inside the extruder. Lowering the temperature to the critical temperature will cause some of the reversible cross-links to re-cross-link and begin to form a gel-like composition. In some exemplary embodiments, lowering the temperature of the polymeric melt while the melt is inside the extruder improves the melt strength of extrusion composition.

Figure 2:
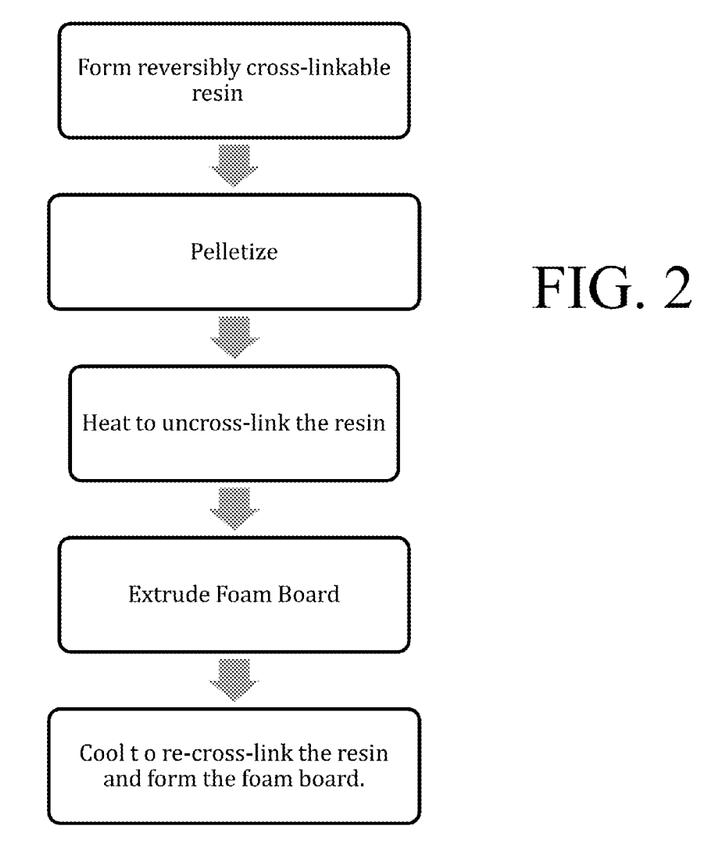
FIG. 2 is an exemplary process for forming reversibly cross-linkable foam.
Figure 3:
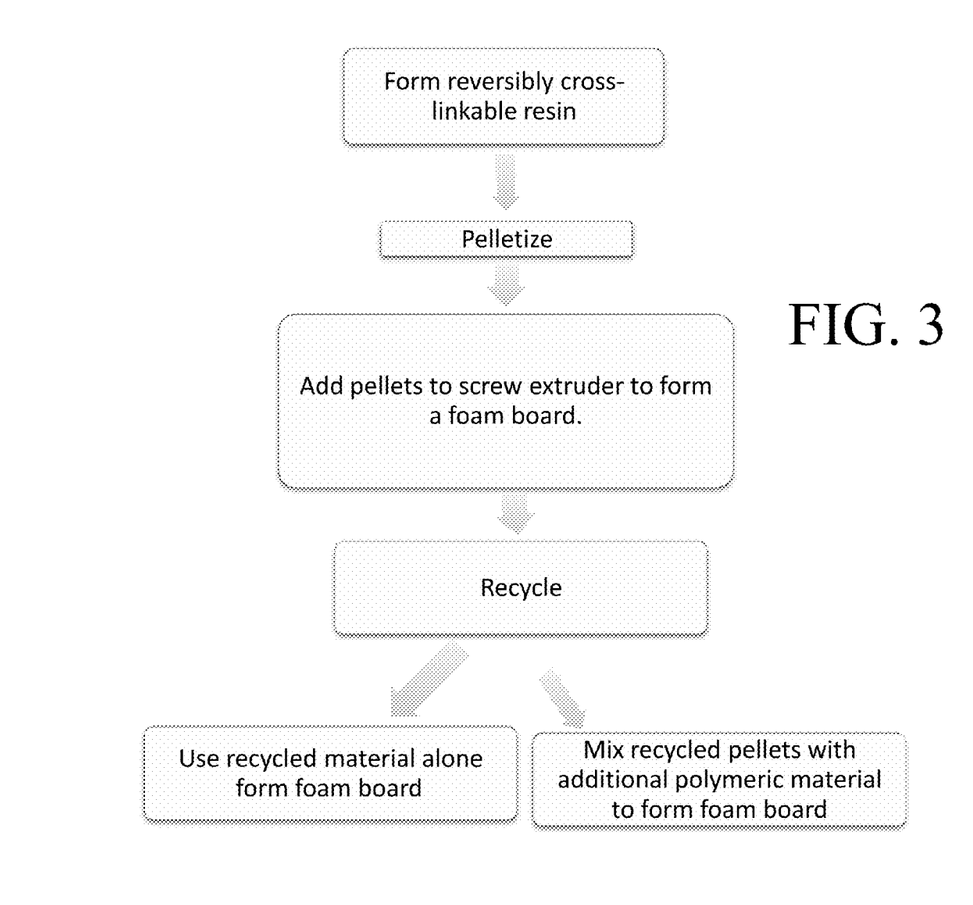
FIG. 3 is another exemplary process for forming and recycling reversibly cross-linkable foam.

FIGS. 2 and 3 illustrate exemplary methods for using the subject reversibly cross-linkable resin in the production of foam boards. As illustrated in FIG. 2, once the reversibly cross-linkable resin is faulted, the resin may be pelletized by conventional methods for immediate use or to be stored for later use. Pelletizing the molten reversible cross-linkable resin cools the resin to a point below a critical temperature, thus causing the resin to cross-link. The cross-linked pellets may then be added to a screw extruder through a feed hopper and melted, such that the cross-links are broken, again forming a reversibly cross-linkable melt. The reversibly cross-linkable melt may be used alone as the extrusion composition, or it may be mixed with an additional polymeric material to produce the extrusion composition. This extrusion composition may then be forced through an extrusion die to produce polymeric foam.

As illustrated in FIG. 3, in some exemplary embodiments, the reversibly cross-linkable monomers or polymers present in the foam allow the foam to be recycled, in which the foam is ground and melted, thereby breaking the reversible cross-links. This recycled polymeric material may then be cooled and pelletized, which in turn re-forms the reversible cross-links. The recycled pellets may then be incorporated into a screw extruder alone, or the recycled pellets may be mixed with other polymeric material to form a polymeric foam board.

The foam composition produces rigid, substantially closed cell, polymer foam boards prepared by an extruding process. In some exemplary embodiments, the inventive copolymer composition provides a reversibly cross-linked structure while at least maintaining the desired physical and thermal properties. For instance, the copolymer material is capable of producing substantially closed cellular foams with an average density of about 1.0 lbs/ft$^3$ to about 6.0 lbs/ft$^3$, or from about 1.2 lbs/ft$^3$ to about 3.5 lbs/ft$^3$. In some exemplary embodiments, the foam has an average density of about 1.4 lbs/ft$^3$ to about 2.0 lbs/ft$^3$. It is to be appreciated that the phrase "substantially closed cell" is meant to indicate that the foam contains all closed cells or nearly all of the cells in the cellular structure are closed. In most exemplary embodiments, not more than 30.0% of the cells are open cells, and particularly, not more than 10.0%, or more than 5.0% are open cells, or otherwise "non-closed" cells. The closed cell structure helps to increase the R-value of a formed, foamed insulation product.

It is to be appreciated, however, that it is within the purview of the present invention to produce an open cell structure. Accordingly, in some exemplary embodiments, the copolymer material is capable of producing substantially open cellular foams.

Additionally, the copolymer foamable material may produce extruded foams that have a higher compressive strength than conventional extruded polystyrene foams. The compressive strength defines the capacity of a foam material to withstand axially directed pushing forces. Conventional extruded polystyrene foams that do not include a reversibly cross-linked polymeric material generally demonstrate compressive strengths of from about 6 to 100 psi. In some exemplary embodiments, the foamable polymeric materials with reversible cross-links disclosed herein are capable of producing foams with an increased compressive strength of at least 10% or more over otherwise identical foam compositions that do not include the reversibly cross-linkable materials.

In some exemplary embodiments, by including the reversibly cross-linkable copolymers, as disclosed herein, the resulting extruded foam demonstrates improvements in at least one of the following properties: heat deflection temperature, shear strength, flexural strength, flexural modulus, compressive strength, compressive modulus, tensile strength, and tensile modulus. In some exemplary embodiments, the foamable polymeric materials with reversible cross-links disclosed herein are capable of producing foams with properties that improve by at least 10% as compared to otherwise identical foam compositions that do not include the reversibly cross-linkable materials.

In some exemplary embodiments, the foamable polymeric material is capable of producing extruded polystyrene foams with increased service temperatures, as compared to conventional extruded polystyrene foams. Higher service temperatures allow the foam to maintain its properties at these high temperatures without degrading. Conventional extruded polystyrene foams demonstrate temperature ranges of about 150° F. to 180° F. and are limited by the temperature at which the polymer molecules begin to move. Cross-linking the polymer reduces this movement and increases the glass transition temperature (Tg). In some exemplary embodiments, the reversibly cross-linked polymer foam has a service temperature of at least about 200° F. In some exemplary embodiments, the reversibly cross-linked polymer foam has a service temperature of at least about 210° F. or at least about 225° F.

Higher service temperatures for polystyrene-based foams opens up new markets for polystyrene foams that require high temperatures, such as roofing, wind blade, HVAC, and the like. For example, the reversible cross-linkable extruded polystyrene foams may be useful for above and below grade exterior insulation, fabrication billets, low density geo filler, and automotive applications.

In some exemplary embodiments, the foamable polymeric material produces foams that have insulation values (R-values) of about 4.0-7.0 per inch. In at least one embodiment, the R-value is 5.0 per inch. In addition, the average cell size of the inventive foam and foamed products is 0.005 mm (5 microns) to 0.6 mm (600 microns) and, in some embodiments, from 0.160 mm (160 microns) to 0.200 mm (200 microns). The extruded inventive foam may be formed into an insulation product such as rigid insulation boards, insulation foam, packaging products, and building insulation or underground insulation (for example, highway, airport runway, railway, and underground utility insulation).

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

The invention claimed is:

1. A reversibly cross-linked foam comprising:
a blowing agent;
a first polymeric material; and
at least one reversibly cross-linkable agent polymerized with said first polymeric material, forming a reversibly cross-linkable copolymer,
wherein said reversibly cross-linkable agent comprises a metal-ligand complex ion and the ligand is at least one of a polyester (meth)acrylate and a polyurethane (meth)acrylate, and
wherein said reversibly cross-linked foam is thermally stable at temperatures of at least 10° F. higher than an otherwise identical foam that does not include the reversibly cross-linkable agent.

2. A reversibly cross-linked foam comprising:
a blowing agent;
a first polymeric material; and
at least one reversibly cross-linkable agent polymerized with said first polymeric material, forming a reversibly cross-linkable copolymer,
wherein said reversibly cross-linkable agent comprises a metal-ligand complex ion,
wherein said metal-ligand complex ion comprises a terpyridine ligand reacted with a metal ion, and
wherein said reversibly cross-linked foam is thermally stable at temperatures of at least 10° F. higher than an otherwise identical foam that does not include the reversibly cross-linkable agent.

3. The reversibly cross-linked foam of claim 1, wherein said first polymeric material comprises an alkenyl aromatic polymer.

4. The reversibly cross-linked foam of claim 3, wherein said alkenyl aromatic polymer is derived from one or more of styrene, α-methylstyrene, ethylstyrene, vinyl benzene, vinyl toluene, chlorostyrene, and bromostyrene.

5. The reversibly cross-linked foam of claim 1, wherein said reversibly cross-linkable copolymer is further blended with a second polymeric material prior to or during formation of said reversibly cross-linked foam.

6. The reversibly cross-linked foam of claim 5, wherein said second polymeric material is one or more of alkenyl aromatic polymers, polyvinyl chloride ("PVC"), chlorinated polyvinyl chloride ("CPVC"), polyethylene, polypropylene, polycarbonates, polyisocyanurates, polyetherimides, polyamides, polyesters, polycarbonates, polymethylmethacrylate, polyphenylene oxide, polyurethanes, phenolics, polyolefins, styrene acrylonitrile ("SAN"), acrylonitrile butadiene styrene, acrylic/styrene/acrylonitrile block terpolymer ("ASA"), polysulfone, polyphenylene sulfide, acetal resins, polyaramides, polyimides, polyacrylic acid esters, copolymers of ethylene and propylene, copolymers of styrene and butadiene, copolymers of vinylacetate and ethylene, rubber modified polymers, thermoplastic polymer blends, and combinations thereof.

7. The reversibly cross-linked foam of claim 1, wherein said blowing agent includes one or more of an HFO, HFC, HCFO, and $CO_2$.

8. The reversibly cross-linked foam of claim 7, wherein said blowing agent is included in an amount from about 1.0 to 15.0 weight percent of the foamable composition.

9. The reversibly cross-linked foam of claim 1, further including at least one infrared attenuating agent.

10. The reversibly cross-linked foam of claim 1, further including one or more of an infrared attenuating agent, a nucleating agent, a plasticizing agent, a fire retardant, a pigment, an elastomer, an extrusion aid, an antioxidant, a filler, an antistatic agent, a biocide, and/or a UV absorber.

11. The reversibly cross-linked foam of claim 2, wherein said first polymeric material comprises an alkenyl aromatic polymer.

12. The reversibly cross-linked foam of claim 11, wherein said alkenyl aromatic polymer is derived from one or more of styrene, α-methylstyrene, ethylstyrene, vinyl benzene, vinyl toluene, chlorostyrene, and bromostyrene.

13. The reversibly cross-linked foam of claim 2, wherein said reversibly cross-linkable copolymer is further blended with a second polymeric material prior to or during formation of said reversibly cross-linked foam.

14. The reversibly cross-linked foam of claim 13, wherein said second polymeric material is one or more of alkenyl aromatic polymers, polyvinyl chloride ("PVC"), chlorinated polyvinyl chloride ("CPVC"), polyethylene, polypropylene, polycarbonates, polyisocyanurates, polyetherimides, polyesters, polycarbonates, polymethylmethacrylate, polyphenylene oxide, polyurethanes, phenolics, polyolefins, styrene acrylonitrile ("SAN"), acrylonitrile butadiene styrene, acrylic/styrene/acrylonitrile block terpolymer ("ASA"), polysulfone, polyphenylene sulfide, acetal resins, polyamides, polyaramides, polyimides, polyacrylic acid esters, copolymers of ethylene and propylene, copolymers of styrene and butadiene, copolymers of vinylacetate and ethylene, rubber modified polymers, thermoplastic polymer blends, and combinations thereof.

15. The reversibly cross-linked foam of claim 2, wherein said blowing agent includes one or more of an HFO, HFC, HCFO, and $CO_2$.

16. The reversibly cross-linked foam of claim 15, wherein said blowing agent is included in an amount from about 1.0 to 15.0 weight percent of the foamable composition.

17. The reversibly cross-linked foam of claim 2, further including at least one infrared attenuating agent.

18. The reversibly cross-linked foam of claim 2, further including one or more of an infrared attenuating agent, a nucleating agent, a plasticizing agent, a fire retardant, a pigment, an elastomer, an extrusion aid, an antioxidant, a filler, an antistatic agent, a biocide, and/or a UV absorber.

* * * * *